United States Patent [19]

O'Neil et al.

[11] Patent Number: 5,993,415
[45] Date of Patent: Nov. 30, 1999

[54] CROSSLINKED NYLON BLOCK COPOLYMERS

[75] Inventors: Charles J. O'Neil, Chelmsford, Mass.; Lawrence A. Acquarulo, Jr., Lisbon, Conn.

[73] Assignee: Lawrence A. Acquarulo, Dayville, Conn.

[21] Appl. No.: 09/108,915

[22] Filed: Jul. 1, 1998

Related U.S. Application Data

[62] Division of application No. 08/867,362, Jun. 2, 1997.

[51] Int. Cl.$^6$ .......................... A61M 25/00; A61M 25/10; C08J 3/24
[52] U.S. Cl. .......................... 604/96; 604/264; 604/523; 604/524; 522/137
[58] Field of Search .............................. 525/137; 604/96, 604/264, 523, 524

[56] References Cited

U.S. PATENT DOCUMENTS

| | | | |
|---|---|---|---|
| 4,031,164 | 6/1977 | Hedrick et al. | 260/857 |
| 4,444,816 | 4/1984 | Richards et al. | 428/36 |
| 4,451,641 | 5/1984 | Sublett et al. | 528/295.5 |
| 4,460,445 | 7/1984 | Rekers | 204/159.2 |
| 4,546,152 | 10/1985 | Koelmel et al. | 525/437 |
| 4,617,355 | 10/1986 | Gabbert et al. | 525/420 |
| 4,624,972 | 11/1986 | Nace | 523/136 |
| 5,198,551 | 3/1993 | Benicewicz et al | 548/435 |
| 5,296,556 | 3/1994 | Frihart | 525/420.5 |
| 5,315,011 | 5/1994 | Benicewicz et al. | 548/521 |
| 5,584,821 | 12/1996 | Hobbs et al. | 604/280 |

FOREIGN PATENT DOCUMENTS

| | | |
|---|---|---|
| 0149986 | 7/1985 | European Pat. Off. . |
| 0189583 | 8/1986 | European Pat. Off. . |
| 0345649 | 12/1989 | European Pat. Off. . |

OTHER PUBLICATIONS

Richter et al., "Flexible Polyurethan Cables"; 1993; pp. 939–943; ANTEC.

Skiens et al.; "Ionizing Radiation's Effects on Selected Biomedical Polymers"; date unknown; pp. 1001–1018; Chapter 44 of Biocompatible Polymers, Metals, and Composites; Society of Plastics Enginerrs, Inc.

Lundy et al.; "Methods of Color Stabilization in Gamma Radiation Sterilized Polycarbonate"; 1988; pp. 1349–1351; ANTEC.

Zamore et al.; "Crosslinkable Thermoplastic Polyurethane"; Sep. 1996; p. 50; Wire Technology International.

Chinese Journal of Polymer Science, vol. 7, No. 1 Feng et al; "Characterization of γ–Irradiated Crystalline Polymers II Isothermal Crystallization Kinetics of γ–Radiation induced Crosslined Polyamide 1010"; 1989; pp.54–65.

E.V. Gorbunova; "Production and Properties of Crosslinked Compositions of Aliphatic Polyamides"; 1993; Plast.Massy, No. 2, 1993; pp.35–37; (In Russian).

Author unknown; "Test Method For Measurement of Hot Creep of Polymeric Insulations"; 1984; pages unknown; Insulated Cable Engineers Association, Inc.

*Primary Examiner*—Patricia A. Short
*Attorney, Agent, or Firm*—Hayes, Soloway, Hennessey Grossman & Hage PC

[57] ABSTRACT

A crosslinked nylon block copolymer comprising a copolymer containing a polyamide block and an elastomeric block, irradiation crosslinked, including a compound which promotes crosslinking therein. In process form, the present invention comprises supplying a nylon block copolymer, containing a polyamide block and an elastomeric block, along with crosslinking promotor and exposing the block copolymer to irradiation, sufficient to crosslink the copolymer and improve mechanical properties therein. The crosslinked nylon block copolymers here have particular utility in both the medical and wire and cable industries.

21 Claims, No Drawings

CROSSLINKED NYLON BLOCK COPOLYMERS

This is a divisional of copending application Ser. No. 08/867,362 filed on Jun. 2, 1997, pending.

FIELD OF THE INVENTION

The present invention relates to the preparation of crosslinked nylon block copolymer materials, and to their use in medical applications, particular as a component for the preparation of a rigidized stem section for a catheter or other similar medical device. In addition, the crosslinked nylon block copolymer materials herein have utility in the wire and cable industry.

BACKGROUND OF THE INVENTION

Generally, nylon block copolymers may be alternating blocks of polyamide segments and other segments such as segments of elastomeric polymers such as polyethers, polyesters, hydrocarbons or polysiloxanes. These nylon block copolymers are generally prepared by copolymerizing a lactam monomer in the present of the elastomeric polymers component. A more detailed discussion of the structure and method of preparing particular types of nylon block copolymers can be found in U.S. Pat. No. 4,031,164.

The polyamide segments and elastomeric polymer segments of the nylon block copolymers each contribute to the respective properties of the final polymer. In order to obtain high modulus materials, polyamide segments of higher molecular weight and/or higher weight percent can be employed. Alternatively, greater tensile elongation and impact properties, as well as lower surface hardness, may be obtained by using higher percents of and/or higher molecular weight elastomeric polymer component.

U.S. Pat. No. 4,671,355 appears to be one of the first disclosures of a crosslinked nylon block copolymer, chemically, through the use of polyfunctional amine compounds. That is, the crosslinked nylon block copolymers are prepared by a reaction scheme in which polyfunctional amines act as crosslinking agents. More specifically, a crosslinked material was reportedly synethesized by reacting an acyl lactam functionalized material with the polyfunctional amine to prepare crosslinked acyl lactam materials which were then concurrently or subsequently reacted with lactam monomer in the presence of a lactam polymerization catalyst to form the crosslinked nylon block copolymer material. It was reported therein that by chemically crosslinking, it was discovered that the overall properties of the final polymer could be varied even if one maintains the molecular weight and weight percent of the elastomeric polymer component.

While the above chemical method of crosslinking a nylon block copolymer has been reported, no reports exist concerning the development of a nylon block copolymer by a more convenient method such as irradiation. The closest attempts in this regard can be found, for example, in Plast. Massy, 1993, No. 2, pp 35–37, which contains a paper entitled "Production and Properties of Crosslinked Compositions of Aliphatic Nylons". According to the abstract, a study was conducted on the process of radiation crosslinking of an aliphatic polyamides (i.e., not a nylon block copolymers) and an assessment is made of the properties and network compositions obtained. The materials studied were nylon-6, nylon-6,6 and nylon-12. The polyfunctional monomers employed to accelerate crosslinking were triallyl cyanurate and triallyl isocyanurate. Mechanical data is supplied.

Similarly, in the Chinese Journal of Polymer Science, Vol. 7, No. 1, there is a paper entitled "Characterization of Irradiated Crystalline Polymer-Isothermal Crystallization Kinetics of Radiation Induced Crosslinked Polyamide 1010". As disclosed therein, after irradiation, the service temperature of the resin is raised to about 240° C. In addition, network formation is said to greatly change the crystallization behavior of the otherwise crystalline polyamide material.

Finally, it is worth noting that various other disclosures have been uncovered, which recite thermoset (or crosslinked) polyamide resins, but again, no mention or suggestion of irradiation crosslinking of a nylon block copolymer is described. For example, in U.S. Pat. No. 5,198,551 entitled "Polyamide Thermosets" there is disclosed what is termed curable polyamide monomers, curable liquid crystal polyamide monomers and thermoset compositions prepared therefrom. The theremoset polyamides so prepared all contained highly aromatic type structure. Similarly, in U.S. Pat. No. 5,3154,011, which is a divisional of the '551 patent, there is again described curable polyamide monomer systems, which monomers represent highly aromatic type functionality.

The fact that there have been no reports concerning the development of a convenient route for the preparation of a crosslinked nylon block copolymer is underscored when reference is made to U.S. Pat. No. 5,584,821, which discloses an angiographic catheter which has a relatively stiff though flexible shaft and a soft tip. The soft tip consists primarily of a tungsten loaded polyether block amide (PEBA) copolymer surrounded by two thin PEBA layers. This three ply radiopaque tip is bonded to a PEBA shaft. The shaft is reinforced either by an inner nylon ply or by metal braiding.

In other words, pursuant to the teachings of U.S. Pat. No. 5,584,821 when it comes to the production of a soft tip catheter with a relatively stiffer body, the teachings therein emphasize that the stiffer body portion relies upon the use of a metal braided reinforced copolymer or a co-extruded two ply wall consisting of nylon and PEBA copolymer. That being the case, it becomes clear that inasmuch as PEBA type copolymers are widely used in catheter type applications, it would serve a long-standing need if one could conveniently produce a more rigid and toughened PEBA catheter, without the need for the structural modifications emphasized in the prior art.

Accordingly, it is an object of this invention to prepare a crosslinked nylon block copolymer, wherein said polymer is conveniently crosslinked by the process of irradiation or other high energy source, wherein such crosslinked nylon block copolymer has particular utility as a component of a medical catheter product.

More specifically, it is object of the present invention to prepare a crosslinked nylon block copolymer elastomeric formulation, via irradiation techniques, wherein the elastomeric composition, subsequent to crosslinking, exhibits improvement in properties such as mechanical strength, heat resistance, and hardness, and in particular, the crosslinked material so produced demonstrates elongational behavior when exposed to elevated temperatures under conditions of constant stress.

Furthermore, it is an object of the present invention to crosslink nylon block copolymer systems, wherein such crosslinking improves the overall elastomeric toughness of the block copolymer, thereby providing what can be termed a much more durable nylon block copolymer product for a variety of miscellaneous applications in the medical industry.

SUMMARY OF THE INVENTION

A crosslinked nylon block copolymer comprising a copolymer containing a polyamide block and an elastomeric block, irradiation crosslinked, including a compound which promotes crosslinking therein. In process form, the present invention comprises supplying a nylon block copolymer, containing a polyamide block and an elastomeric block, along with crosslinking promotor and exposing said block copolymer to irradiation, sufficient to crosslink said block copolymer and improve mechanical properties therein, particularly the ability of said block copolymer to elongate upon exposure to a constant load of about 29 psi at an elevated temperature of about 200° C. for 15 min.

DETAILED DESCRIPTION OF THE PREFERRED EMBODIMENTS

As noted above, the present invention in composition form relates to a an irradiation-crosslinked nylon block copolymer. Preferably, the nylon block copolymer is a nylon block copolymer sold by ATOCHEM under the tradename PEBAX® which is a elastomeric type nylon block copolymer. The commercial PEBAX polymers consist of polyether blocks separated by polyamide blocks. The polyether blocks may be based upon polyethylene glycol, polypropylene glycol, or polytetramethylene ether glycol. The polyamides are usually based upon nylon-11 but may be based upon nylons 6 of nylon-6,6 or even a copolymer such as nylon-6/nylon-11. A wide range of block polyamides have been offered and vary in the type of polyether, the nature of the polyamide block and the ratio of polyether to polyamide blocks. The polymers range in hardness from Shore A 60 to Shore D72 which is broader than for the thermoplastic polyester and thermoplastic polyurethane rubbers. Melting range is also dependent on the particular composition, and varies between 140–215° C.

The above nylon block copolymers have been found to undergo crosslinking upon exposure to irradiation. Listed below in Table I are the results of various exposure levels as applied to a PEBAX Shore 72A material, containing 2.0% TAIC (triallylisocyonurate) and the corresponding changes in mechanical properties observed:

TABLE I

| | 0 MR | 5 MR | 10 MR | 15 MR | 20 MR |
|---|---|---|---|---|---|
| T.S. (psi) | 8,632 | 10,531 | 7,751 | | |
| Yield (psi) | 4,026 | 4,979 | 5,186 | | |
| 100% Mod (psi) | 3,498 | 4,035 | 4,216 | | |
| Elong (%) | *404.2 | *358.3 | *283.3 | ** | ** |
| Creep (%) | *** | 54.3 | 61.4 | 58.3 | 63.0 |
| Set (%) | — | 1.5 | 4.1 | 3.6 | 4.6 |

*Necked
**NOTE: The 15 mr and 20 mr samples necked and there was very little elongation (less than ¼ inch).
***At 200° C., the unexposed material melted. At 150° C. the unexposed material elongated 1/32 inch (3.1%). At 175° C. it broke in the clamp, but did not melt. The sample elongated 5/8 inch (62.5%) before it broke.

One of the more relevant properties reported on in Table I, is the % Creep which was measured at 200° C., 29 psi, over a 15 minute period. This is formally known as the "Test Method for Measurement of Hot Creep of Polymeric Insulations", Publication T-28-562, published by the Insulated Cable Engineers Association, Inc, of South Yarmouth, Mass. In accordance with the present invention, elongations of less than 100% are preferred, and most preferred is an elongation of about 10–65%.

As can be seen, unexposed PEBAX actually melted under these conditions of testing, and no elongation was observed. By contrast, after a 5 megarad total exposure, the percent creep is about 54.6%. In other words, irradiation clearly promotes crosslinking and network formation within the nylon block copolymer material, and as a thermoset, it no longer melts and flow, and elastomeric behavior is observed.

Also, as can be seen from Table I, exposure to 5 megarads results in an associated drop in the percent of elongation from about 404% to about 358%, which is a characteristic expected due to crosslinking. In addition, exposure at 5 megarads increases the tensile strength from about 8600 psi to about 10,500 psi, which is again a result of network crosslink formation.

As can also be seen in Table I, while an exposure of 5 megarads along with about 2.0% of a promotor ("TAIC" or "TAC", triallylcyanurate) provides optimum composition and conditions, higher exposure levels are still acceptable. For example, a total exposure of 10 megarads similarly provides a sample that elongates about 61% after exposure to 29 psi, at 200° C. for 15 minutes. However, with respect to this particular sample, it is worth pointing out that the tensile strength drops to about 7750 psi, which may be the onset of some degradation. Upon exposure to even higher total levels of irradiation (15 and 20 megarads) the sample still demonstrates elongational values of about 58 and 63%, respectively, however, at such total exposure levels, the samples necked and their was very little elongation at room temperature. Again, this is believed to be the result of the degradation that may take place when total irradiation becomes too high.

With regards to the specific utility of the invention disclosed herein, it is noted that the crosslinked nylon block copolymer disclosed herein has utility in both the medical products field, as well as in the wire and cable industry.

More specifically, when it comes to the production of an intravascular flexible catheter having a tubular shaft comprising a nylon block copolymer, and a soft flexible tubular tip distal of and bonded to said shaft, the improvement recited herein comprises irradiation crosslinking said nylon block copolymer of said shaft, wherein said crosslinking increases the rigidity of said shaft relative to said soft flexible distal tip. In addition, in the balloon catheter field, in the case of such catheters manufactured from a nylon block copolymer, the invention herein provides for the preparation of a balloon type catheter, wherein the balloon section relative to the shaft can be converted into a thermoset or crosslinked type structure, thereby increasing its overall mechanical strength, performance, and durability.

Accordingly, the compositions and method disclosed herein provide a much more convenient route for the preparation of a novel rigid-flex nylon block copolymer resin, particularly suited for the production of novel type catheter products, without the need for structural modification of the catheter type systems as disclosed and emphasized by the prior art. In addition, the compositions herein are well-suited as an electrical insulating material for the wire and cable industry.

We claim:

1. In an intravascular flexible catheter having a tubular shaft comprising a nylon block copolymer, and a soft flexible tubular tip distal of and bonded to said shaft, the improvement comprising irradiation crosslinking said nylon block copolymer of said tubular shaft, wherein said crosslinking increases the rigidity of said shaft relative to said soft flexible distal tip.

2. In a catheter according to claim 1, the improvement wherein the crosslinked nylon block copolymer comprises a copolymer containing a polyamide block and an elastomeric block, irradiation crosslinked, including a compound which promotes crosslinking therein.

3. In a catheter according to claim 2, the improvement wherein said crosslinked nylon block copolymer elongates after about 15 minutes at about 200° C. and about 29 psi.

4. In a catheter according to claim 3, the improvement wherein said elongation is less than about 100%.

5. In a catheter according to claim 4, the improvement wherein said elongation is about 10–65%.

6. In a catheter according to claim 2, the improvement block is selected from a polyether, polyester, hydrocarbon, polysiloxane, or mixtures thereof.

7. In a catheter according to claim 2, the improvement wherein said compound which promotes crosslinking is triallyisocyanurate or triallylcyanurate.

8. In a catheter according to claim 7, the improvement triallylisocyanurate or triallylcyanurate is present at a level of about 2.0% (wt).

9. In a catheter according to claim 2, the improvement wherein said irradiation is less than about 20 megarads.

10. In a catheter according to claim 9, the improvement wherein said irradiation is 5, 10, 15 or 20 megarads.

11. In a balloon type catheter having a tubular shaft comprising a nylon block copolymer and an integrally formed balloon section, the improvement comprising irradiation crosslinking said nylon block copolymer of said balloon section, wherein said crosslinking lowers the percent elongation of said balloon section as compared to the elongation prior to crosslinking.

12. In a catheter according to claim 11, the improvement wherein the crosslinked nylon block copolymer comprises a copolymer containing a polyamide block and an elastomeric block, irradiation crosslinked, including a compound which promotes crosslinking therein.

13. In a catheter according to claim 12, the improvement wherein said crosslinked nylon block copolymer elongates after about 15 minutes at about 200° C. and about 29 psi.

14. In a catheter according to claim 13, the improvement wherein said elongation is less than about 100%.

15. In a catheter according to claim 14, the improvement wherein said elongation is about 10–65%.

16. In a catheter according to claim 12, the improvement block is selected from a polyether, polyester, hydrocarbon, polysiloxane, or mixtures thereof.

17. In a catheter according to claim 12, the improvement wherein said compound which promotes crosslinking is triallyisocyanurate or triallylcyanurate.

18. In a catheter according to claim 17, the improvement triallylisocyanurate or triallylcyanurate is present at a level of about 2.0% (wt).

19. In a catheter according to claim 12, the improvement wherein said irradiation is less than about 20 megarads.

20. In a catheter according to claim 19, the improvement wherein said irradiation is 5, 10, 15 or 20 megarads.

21. A process for preparing a crosslinked nylon block copolymer comprising supplying a copolymer containing a polyamide block and an elastomeric block, mixing a crosslinking promotor into said copolymer, and exposing said copolymer with promotor to irradiation crosslinking.

* * * * *